United States Defensive Publication [19] (H) [11] T973,016

Shull et al. [43] Aug. 1, 1978

[54] CYANOETHYLATION OF HYDANTOINS

[75] Inventors: Samuel Ellsworth Shull, Cogan Station, Pa.; John Douglas Freilich, Grand Island, N.Y.

[73] Assignee: Glyco Chemicals, Inc., Greenwich, Conn.

[21] Appl. No.: 846,019

[22] Filed: Oct. 27, 1977

Related U.S. Application Data

[63] Continuation of Ser. No. 747,987, Dec. 6, 1976, abandoned.

[51] Int. Cl.[2] ..... C07D 233/72

[52] U.S. Cl. ..... 548/312

[57] ABSTRACT

An improved process for the manufacture of a 3-β-cyanoethyl- or a 1,3-di(β-cyanoethyl)-5,5-disubstituted hydantoin, by reacting acrylonitrile and a 5,5-disubstituted hydantoin in the presence of a base catalyst in a solvent media composed of a secondary and/or tertiary alcohol having up to 5 carbon atoms and a boiling point from between about 80°–135° C as a reaction solvent. The alcohol reaction solvent may be used for crystallization of the cyanoethylated product.

The solvent media can for example be selected from the group of isopropanol, 2-methyl-2-butanol, 3-methyl-2-butanol, 2-pentanol, 3-pentanol, tertiary butanol, 1,1-dimethylpropanol and mixtures thereof. The process provides for obtaining high yields of pure product with the formation of a minimum of side reactions and by-products.

10 Claims, No Sheets Drawing,

18 Pages Specification

The file of this unexamined application may be inspected and copies thereof may be purchased (849 O.G. 1221, Apr. 9, 1968).